United States Patent
Pichardo et al.

(10) Patent No.: US 7,806,337 B2
(45) Date of Patent: Oct. 5, 2010

(54) SYSTEM FOR MANAGING MEMORY STORING DATA IN ONE OR MORE WIRELESS TRANSCEIVER DEVICES

(75) Inventors: Roman E. Pichardo, Medford, MA (US); Dina Lynn LaTulippe, Methuen, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 834 days.

(21) Appl. No.: 11/671,059

(22) Filed: Feb. 5, 2007

(65) Prior Publication Data

US 2007/0181694 A1    Aug. 9, 2007

Related U.S. Application Data

(60) Provisional application No. 60/765,556, filed on Feb. 6, 2006.

(51) Int. Cl.
*G06K 7/10* (2006.01)
(52) U.S. Cl. .................. 235/472.01; 235/462.45; 235/462.46; 235/440
(58) Field of Classification Search ............ 235/472.01, 235/375, 462.46, 462.45, 472.03, 440
See application file for complete search history.

(56) References Cited

U.S. PATENT DOCUMENTS

| | | | |
|---|---|---|---|
| 6,330,436 B1 | 12/2001 | Zidel | |
| 7,278,579 B2 * | 10/2007 | Loffredo et al. | 235/462.46 |
| 2002/0119800 A1 | 8/2002 | Jaggers et al. | |
| 2002/0170823 A1 | 11/2002 | Housefield | |
| 2003/0172218 A1 | 9/2003 | Scott et al. | |
| 2003/0225939 A1* | 12/2003 | Ying et al. | 710/1 |
| 2004/0127210 A1* | 7/2004 | Shostak | 455/422.1 |
| 2004/0147818 A1 | 7/2004 | Levy et al. | |
| 2007/0002533 A1* | 1/2007 | Kogan et al. | 361/686 |

FOREIGN PATENT DOCUMENTS

| WO | WO 00/42911 A | 7/2000 |
|---|---|---|
| WO | WO 02/063541 A | 8/2002 |

* cited by examiner

*Primary Examiner*—Edwyn Labaze
(74) *Attorney, Agent, or Firm*—Jack Schwartz & Associates, PLLC

(57) ABSTRACT

A system manages memory storing data in one or more wireless transceiver devices. A docking station receptacle receives, and makes electrical connection with, a transceiver device used for storing and wirelessly communicating data to a remote location. A docking detector generates a docking signal in response to detecting insertion of a transceiver device into the docking station receptacle. A memory management processor generates a signal for initiating deletion of data from memory in a particular transceiver device inserted in the receptacle in response to a docking signal indicating insertion of the particular transceiver device into the docking station receptacle.

17 Claims, 2 Drawing Sheets

SYSTEM FOR MANAGING MEMORY STORING DATA IN ONE OR MORE WIRELESS TRANSCEIVER DEVICES

CROSS-REFERENCED TO RELATED APPLICATIONS

This is a non-provisional application of U.S. Provisional Application Ser. No. 60/765,556 filed Feb. 6, 2006.

FIELD OF THE INVENTION

The present invention relates to systems for managing memory storing data in wireless transceiver devices, and more particularly to systems for terminating use of a transceiver device and preparing it for use for a new session.

BACKGROUND OF THE INVENTION

Wireless data gathering devices may be used in many environments. For example, they may be used in warehouses for gathering data related to the goods being received and shipped out of the warehouse. They may also be used for performing inventory in warehouse or merchant facilities. They may also used in medical environments for gathering medical data from patients.

Such a wireless data gathering device may be implemented as a transceiver device including memory for storing data received by the device. In a warehouse or merchant environment, data may be entered by a user checking shipments into and/or out of in a warehouse, and/or for determining goods-on-hand during inventory. In a medical facility, such as a hospital, the wireless transceiver data gathering device may include electrodes to be attached to a patient and circuitry to derive data representing patient medical parameters (e.g. EKG, temperature, $SpO_2$, etc.). Data gathered and stored in the transceiver device may be transmitted wirelessly to a remote location, such as a centralized data monitoring system where such data is saved and/or analyzed.

At the end of a use session, the wireless data gathering device is prepared for the next session. This generally includes removing data from the wireless data the wireless data gathering device, recharging the device and preparing the memory for the next session of use. Manual intervention may also be required to delete associated data from the remote location.

In particular, in medical enterprises such as hospitals, when a patient is discharged, the medical monitor is disconnected from the patient. It is required that information related to the previous patient be removed from the monitor and that memory within the monitor be allocated to receive information related to a new patient to which the monitor is to be attached. To do this, a nurse must disconnect the monitor from the patient, and observe and notate (mentally or by written note) the monitor device identifier and/or patient identifier. The nurse then physically navigates through the computer system of the monitor (or the central monitoring station if the monitor is assigned to one) using a trim knob, keyboard and/or mouse, to select and activate a 'discharge' function for that particular monitor device. This requires time and energy of nursing personnel. In addition, in a hectic hospital environment, such as an emergency room, a busy nurse may be interrupted before the completion of the manual intervention required to select the monitor device and remove previous patient information. This function is critical to prepare the monitor for new information to avoid serious consequences which may occur due to merged patient information or inability to monitor patients.

Requiring manual intervention to perform activities which are typically performed at the end of a session is burdensome, error prone, and wastes time and energy of users. A system which can reduce or eliminate the required intervention while preparing the wireless transceiver device (patient monitor) for the next session (patient) is desirable.

BRIEF SUMMARY OF THE INVENTION

In accordance with principles of the present invention, a system manages memory storing data in one or more wireless transceiver devices. A docking station receptacle receives, and makes electrical connection with, a transceiver device used for storing and wirelessly communicating data to a remote location. A docking detector generates a docking signal in response to detecting insertion of a transceiver device into the docking station receptacle. A memory management processor generates a signal for initiating deletion of data from memory in a particular transceiver device inserted in the receptacle in response to a docking signal indicating insertion of the particular transceiver device into the docking station receptacle.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, a system for managing memory in a transceiver device, or other information processing system, for example, in response to user command or input.

Figure 1:
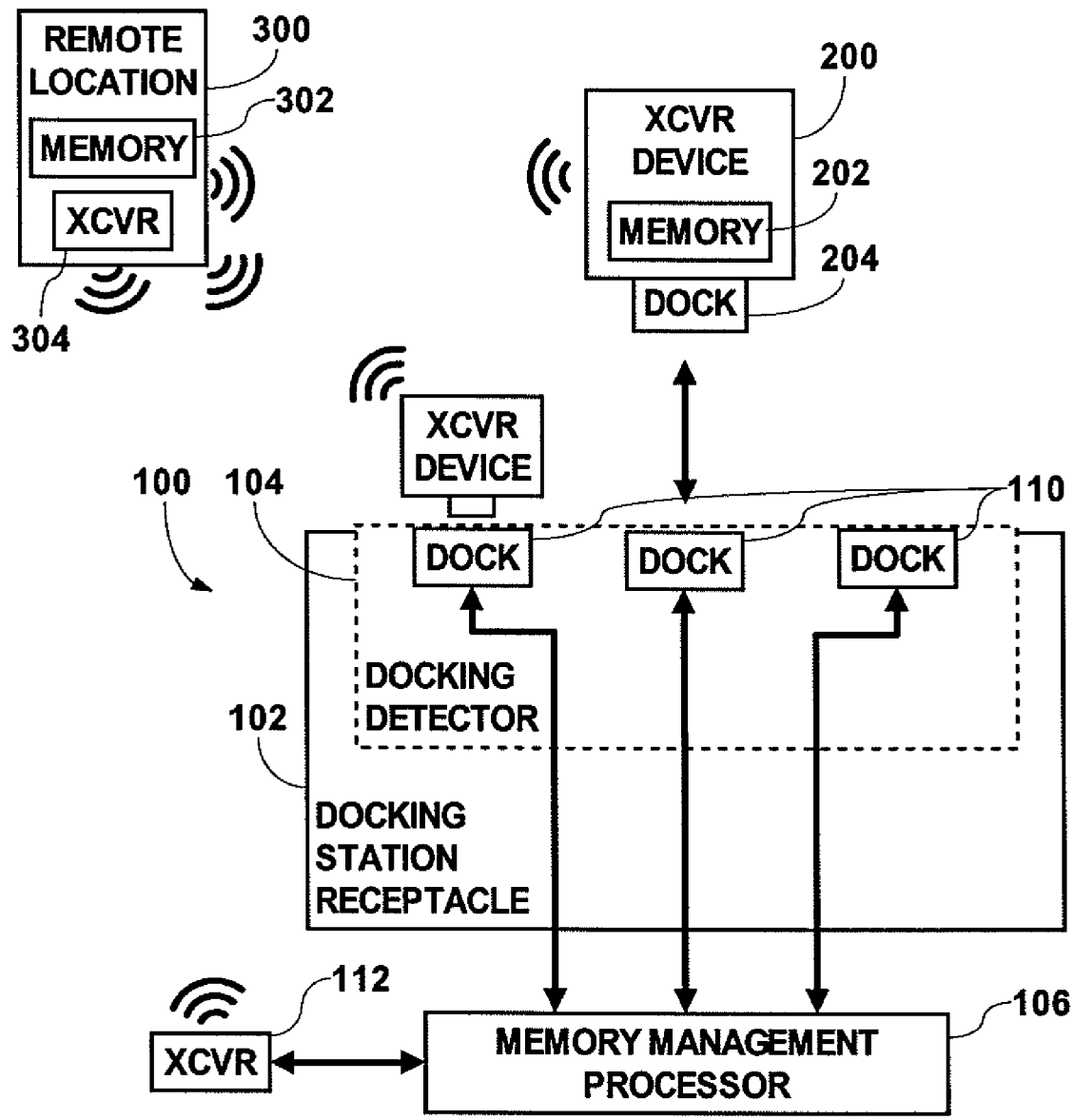
FIG. 1 is a block diagram of a system for managing memory storing data in one or more wireless transceiver devices according to principles of the present invention.

FIG. 1 is a block diagram of a system for managing memory storing data in one or more wireless transceiver devices according to principles of the present invention. In FIG. 1, a transceiver device 200A includes a memory 202 and a docking port 204. A second transceiver device 200B is similar to device 200A but is not illustrated in detail to simplify the drawing. A docking station receptacle 102 includes one or more docking ports 110, corresponding to the docking ports 204 in the wireless transceivers 200. The docking ports 110 interact with a docking detector 104. Respective terminals of the docking ports 110 are bidirectionally coupled to corresponding terminals of a memory management processor 106. The memory management processor 106 is also bidirectionally coupled to a wireless transceiver 112. A remote location 300 includes a memory 302 and a wireless transceiver 304.

In operation, the transceiver devices 200 are used for storing and wirelessly communicating data to the remote location 300. The remote location 300 comprises a centralized data monitoring system for receiving, via the transceiver 304, and storing in the memory 302, data wirelessly received from a plurality of different transceiver devices 200.

The docking station receptacle 102 receives and makes a connection with one or more of the transceiver devices 200 by interconnecting the respective docking ports (204, 110). The docking station receptacle 102 makes connection with the transceiver device 200 by one of: (a) a wired connection via the docking ports 204 and 110, or (b) by wireless coupling via the transceiver device 200 and the transceiver 112. The docking port 110 cooperates with the docking detector 104, which generates a docking signal in response to detecting the insertion of a transceiver device 200 into the docking station receptacle 102. The docking signal is supplied to the memory management processor 106. The docking detector 104 may detect insertion of a transceiver device 200 into the docking station receptacle 102 by one of: (a) an RFID tag and reader means, (b) electrical coupling, and/or (c) magnetic coupling. Other ways to detect insertion of the transceiver device 200 into the docking station receptacle 102 may include optical or mechanical, or other suitable means.

For example, the transceiver device 200 may include an RF identification (RFID) tag and an RFID reader may be implemented in the docking port 110 in the docking station receptacle 102. In this case, when the RFID tag comes within a predetermined distance of the RFID reader, a docking signal is generated by the docking detector 104. Alternatively, electrical coupling, such as by using an electrical connector; or magnetic coupling, such as by using a split core transformer, may be used to detect docking of a transceiver device 200.

The generated docking signal may be one of: (a) an electrical signal if the transceiver device 200 and the docking station receptacle 102 are connected electrically (i.e. by RFID or electrical coupling), and/or (b) a magnetic signal if the particular transceiver device 200 and the docking station receptacle 102 are connected magnetically.

The docking station receptacle 102 may further recharge batteries (not shown) in the transceiver device 200 while the transceiver device 200 is docked. The docking station receptacle 102 recharges the batteries in the transceiver device 200 by one of: (a) electrical coupling, and/or (b) magnetic coupling.

The memory management processor 106 generates a signal for initiating deletion of data stored in the memory 202 of a particular transceiver device 200 inserted in the docking station receptacle 102 in response to the docking signal received from the docking detector 104 indicating insertion of the particular transceiver device 200 into the docking station receptacle 102. This signal is supplied to the particular transceiver device 200. The generated signal for initiating deletion of data from the memory 202 in the particular transceiver device 200 may be (a) a wired signal (e.g. supplied via the bidirectional link between the memory management processor 106, and the docking ports 110 and 204), and/or a wirelessly coupled signal (e.g. supplied via a link between transceivers 12 and the transceiver device 200). The deletion of the data from the memory 202 in the particular transceiver device 200 may be done by one or more of: (a) over-writing (e.g. for electronic read/write memory), (b) magnetic deletion (e.g. for magnetic core memory), and/or (c) UV or other irradiation deletion (e.g. for erasable read-only memory), of the data in the memory 202 of the particular transceiver device 200. Deletion of the data is done automatically upon the memory management processor 106 detecting that a transceiver device 200 is inserted in the docking station receptacle 102, and does not require manual intervention.

In some embodiments, it is necessary for the data in the remote location 300 to be deleted as well. In such embodiments, the docking station receptacle 102 may include a communications interface. In the illustrated embodiment the communications interface is transceiver 112. The communications interface 112 wirelessly communicates a deletion signal to the centralized data monitoring system 300, in response to receipt of a docking signal (indicating insertion of the particular transceiver device 200 into the docking station receptacle 102). The centralized data monitoring system initiates deletion of the data wirelessly received from the particular transceiver device 200 from the memory 302 of the centralized data monitoring system 300 in response to the deletion signal. Alternatively, the particular transceiver 200 may include a communication interface for wirelessly communicating a deletion signal to the centralized data monitoring system 300 to initiate deletion of data wirelessly received from the particular transceiver device 200 from the memory 302 in the centralized data monitoring system 300, in response to a docking signal indicating insertion of the particular transceiver device 200 into the docking station receptacle 102.

In some embodiments, it is desired to allocate locations in the memory 202 in the particular transceiver device 200 in preparation for a subsequent use of the transceiver device 200. In such an embodiment, the memory management processor 106 generates a signal for initiating allocation of the available memory 202 for storage of data in the particular transceiver device 200, and designates the memory used for storing data from the previous use as available for re-use. This may be done in addition to, or instead of, the deletion of data from the memory 202 of the particular transceiver device 200, as described above.

The system described above may be used in any situation where wireless transceiver devices are used to gather data and communicate that data to a remote location, and where data must be deleted from the wireless transceiver devices after a session ends and before a next session begins. For example, the system may be used where the stored data is warehouse and/or inventory data, or where the data is patient medical data.

Figure 2:
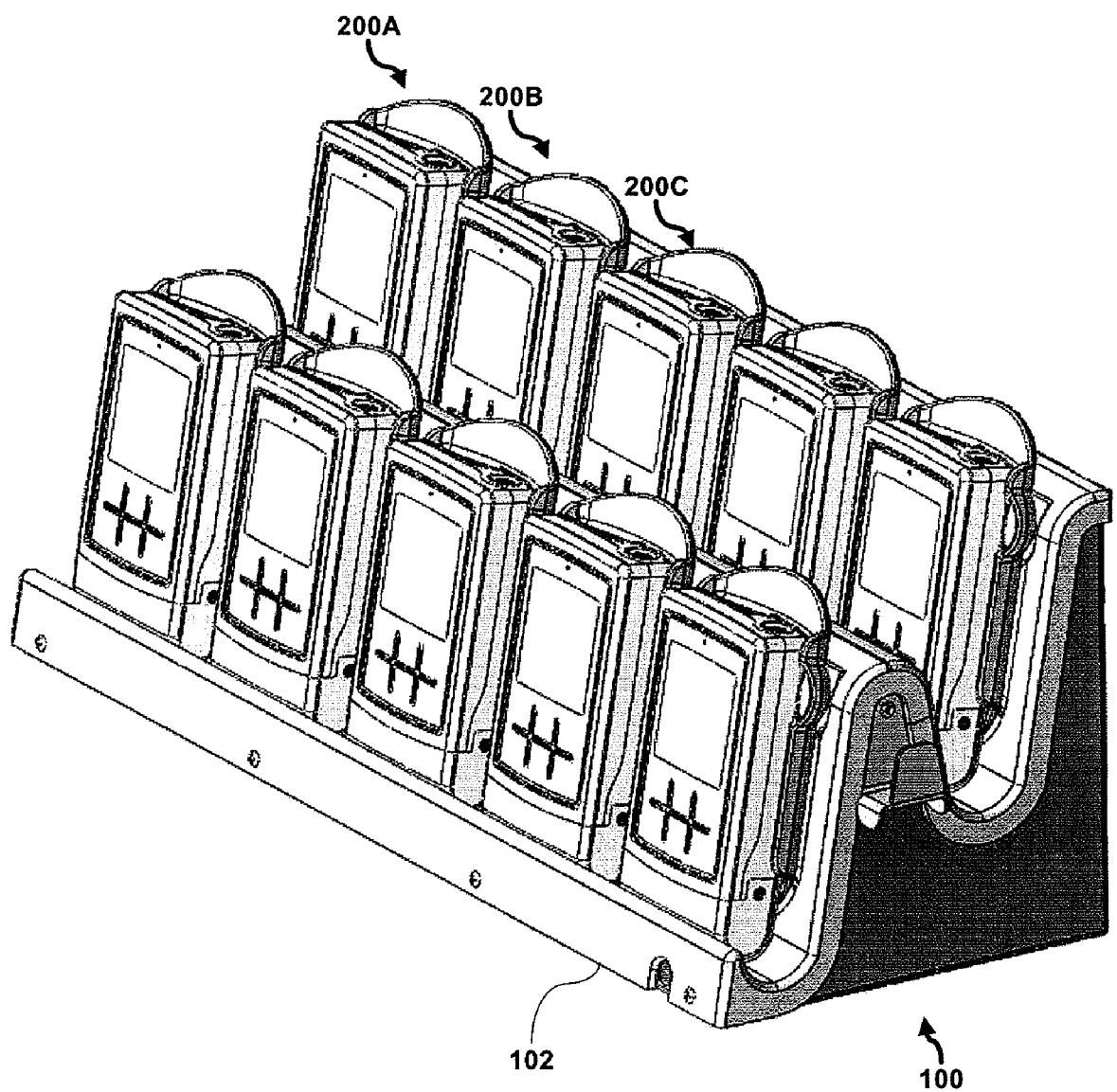
FIG. 2 is an isometric illustration of a portable patient monitor docking station receptacle which may be used in a system according to the present invention.

More specifically, where the data is patient medical data, the system manages memory storing patient medical data in one or more wireless transceiver devices 200 implemented as portable patient monitors. The portable patient monitor transceiver device 200 derives data representing patient physiological parameters, stores that data in the memory 202, and wirelessly communicates that data to the remote location 300, which is a centralized patient data monitoring system for receiving and storing patient medical data wirelessly received from a plurality of portable patient monitor transceiver devices 200. A portable patient monitor docking station is located near a central nursing station. Such a docking station is illustrated in FIG. 2. In FIG. 2, a docking station receptacle 102 includes docking positions for ten portable patient monitor transceiver devices 200A, 200B, 200C and so forth.

Referring to FIG. 1 and FIG. 2, when a patient is discharged, the portable patient monitor transceiver device 200 is disconnected from the patient and inserted in the docking station. The docking station includes a docking station receptacle 102 for receiving and making electrical connection with the portable patient monitor transceiver device 200 used for storing and wirelessly communicating patient medical data to the remote location 300. A docking detector 104 generates a docking signal in response to detecting insertion of a portable patient monitor transceiver device 200 into the docking station receptacle 102. A memory management processor 106 generates a signal for initiating deletion of medical data of a particular patient from the memory 202 in the particular portable patient monitor transceiver device 200 inserted in the docking station receptacle 102 in response to a docking signal indicating insertion of the particular portable patient monitor transceiver device 200 into the docking station receptacle 102. The docking station receptacle 102 also recharges the batteries (not shown) in the portable patient monitor 200.

As described above, the docking station receptacle 102 and/or the particular portable patient monitor transceiver device 200 may include a communication interface for wirelessly communicating a deletion signal to the centralized patient data monitoring system 300 to initiate deletion of medical data of the particular patient wirelessly received from the particular portable patient monitor transceiver device 200 from memory 302 of the centralized patient data monitoring system 300, in response to a docking signal indicating insertion of the particular portable patient monitor transceiver device 200 into the docking station receptacle 102. Also as described above, the memory management processor 106 may generate a signal for initiating allocation of available memory 202 for storage of medical data of a second patient in a particular portable patient monitor transceiver device 200 and designating memory used for storing patient medical data of a previous first patient as available for re-use either in addition to, or in place of, deletion of the patient medical data.

As described above, by automatically initiating deletion of data from a portable patient monitor when it has been disconnected from a patient and placed in a docking station receptacle, without requiring actions by the nursing staff, time and energy is saved and potential errors avoided in hectic environments.

What is claimed is:

1. A system for managing memory storing data in one or more wireless transceiver devices, comprising:
    a docking station receptacle for receiving and making electrical connection with a transceiver device used for gathering, storing and wirelessly communicating data representing patient medical data to a remote location;
    a docking detector for generating a docking signal in response to detecting insertion of a transceiver device into said docking station receptacle; and
    a memory management processor for generating a signal for automatically initiating deletion of stored data representing patient medical data from memory in a particular transceiver device inserted in said receptacle in response to a docking signal indicating insertion of said particular transceiver device into said docking station receptacle;
    wherein the docking station receptacle includes a communication interface for wirelessly communicating a deletion signal to a centralized data monitoring system to initiate deletion of data wirelessly received from said particular transceiver device from memory of said centralized data monitoring system, in response to a docking signal indicating insertion of said particular transceiver device into said docking station receptacle.

2. The system of claim 1 wherein said remote location comprises said centralized data monitoring system for receiving and storing data wirelessly received from a plurality of different transceiver devices.

3. The system of claim 1 wherein the docking station receptacle further recharges batteries in said transceiver device.

4. The system of claim 1 wherein said data is warehouse and/or inventory data.

5. A system according to claim 1 wherein:
    said remote location comprises a centralized patient data monitoring system for receiving and storing patient medical data wirelessly received from a plurality of different transceivers; and said docking station receptacle comprises:
    a communication interface for wirelessly communicating a deletion signal to said centralized patient data monitoring system to initiate deletion of medical data of said particular patient wirelessly received from said particular transceiver device from memory of said centralized patient data monitoring system, in response to a docking signal indicating insertion of said particular transceiver device into said docking station receptacle.

6. A system according to claim 1 wherein said deletion of medical data of said particular patient from said particular transceiver device is performed by at least one of: (a) overwriting, (b) magnetic deletion, and (c) UV or other irradiation deletion, of said medical data of said particular patient.

7. A system according to claim 1 wherein said docking detector detects insertion of a transceiver device into said docking station receptacle by at least one of: (a) an RFID means, (b) electrical coupling, and (c) magnetic coupling.

8. A system according to claim 1 wherein said generated signal for initiating deletion of medical data of a particular patient comprises at least one of: (a) a wired signal, and (b) a wirelessly coupled signal.

9. A system according to claim 1 wherein said generated signal for initiating deletion of medical data of a particular patient comprises at least one of: (a) an electrical signal, and (b) a magnetically coupled signal.

10. A system according to claim 1 wherein said generated docking signal comprises at least one of: (a) an electrical signal, and (b) a magnetically coupled signal.

11. A system according to claim 1 wherein said docking station receptacle makes electrical connection with said transceiver device by at least one of: (a) wired coupling, and (b) wireless coupling.

12. A system according to claim 1 wherein said docking station receptacle re-charges batteries in said transceiver device by at least one of: (a) electrical coupling, and (b) magnetic coupling.

13. A system according to claim 1 wherein said memory management processor further generates a signal for initiating allocation of available memory for storage of medical data of a second patient in a particular transceiver device and designating memory used for storing patient medical data of a previous first patient as available for re-use.

14. A system for managing memory storing data in one or more wireless transceiver devices, comprising:
    a docking station receptacle for receiving and making electrical connection with a transceiver device used for gathering, storing and wirelessly communicating data representing patient medical data to a remote location;
    a docking detector for generating a docking signal in response to detecting insertion of a transceiver device into said docking station receptacle; and
    a memory management processor for generating a signal for automatically initiating deletion of stored data representing patient medical data from memory in a particular transceiver device inserted in said receptacle in response to a docking signal indicating insertion of said particular transceiver device into said docking station receptacle;

wherein said particular transceiver comprises a communication interface for wirelessly communicating a deletion signal to said centralized data monitoring system to initiate deletion of data wirelessly received from said particular transceiver device from memory of said centralized data monitoring system, in response to a docking signal indicating insertion of said particular transceiver device into said docking station receptacle.

15. A system according to claim 14 wherein:

said remote location comprises a centralized patient data monitoring system for receiving and storing patient medical data wirelessly received from a plurality of different transceivers; and said particular transceiver comprises:

a communication interface for wirelessly communicating a deletion signal to said centralized patient data monitoring system to initiate deletion of medical data of said particular patient wirelessly received from said particular transceiver device from memory of said centralized patient data monitoring system, in response to a docking signal indicating insertion of said particular transceiver device into said docking station receptacle.

16. A system for managing memory storing patient medical data in one or more wireless transceiver devices, comprising:

a docking station receptacle for receiving and re-charging a transceiver device used for storing and wirelessly communicating patient medical data to a remote location;

a docking detector for generating a docking signal in response to detecting insertion of a transceiver device into said docking station receptacle; and a memory management processor for generating a signal for initiating deletion of medical data of a particular patient from memory in a particular transceiver device inserted in said receptacle in response to a docking signal indicating insertion of said particular transceiver device into said docking station receptacle;

wherein the docking station receptacle includes a communication interface for wirelessly communicating a deletion signal to a centralized data monitoring system to initiate deletion of data wirelessly received from said particular transceiver device from memory of said centralized data monitoring system, in response to a docking signal indicating insertion of said particular transceiver device into said docking station receptacle.

17. A system for managing memory storing patient medical data comprising:

a transceiver device including circuitry for deriving data representing patient medical parameters;

a docking station receptacle for receiving and re-charging the transceiver device used for storing and wirelessly communicating patient medical data to a remote location;

a docking detector for generating a docking signal in response to detecting insertion of the transceiver device into said docking station receptacle; and a memory management processor for generating a signal for initiating allocation of memory for storage of medical data of a particular patient in the particular transceiver device inserted in said receptacle in response to a docking signal indicating insertion of said particular transceiver device into said docking station receptacle;

wherein the transceiver device includes a communication interface for wirelessly communicating a deletion signal to a centralized data monitoring system to initiate deletion of data wirelessly received from said particular transceiver device from memory of said centralized data monitoring system, in response to a docking signal indicating insertion of said particular transceiver device into said docking station receptacle.

* * * * *